United States Patent [19]
Peters

[11] 3,935,458
[45] Jan. 27, 1976

[54] METHOD FOR MONITORING THE SURFACE RESISTIVITY OF METALLIZED FILM

[75] Inventor: Dan William Peters, Mountain View, Calif.

[73] Assignee: The Sierracin Corporation, Sylmar, Calif.

[22] Filed: Oct. 29, 1974

[21] Appl. No.: 518,904

Related U.S. Application Data

[63] Continuation of Ser. No. 58,305, July 27, 1970, abandoned.

[52] U.S. Cl. .................. 250/338; 250/339; 324/62
[51] Int. Cl.² .......................................... G01J 1/00
[58] Field of Search ........... 250/338, 339, 340, 353, 250/358, 359; 324/62, 58 A; 118/8, 48, 49, 49.1, 49.5

[56] References Cited
UNITED STATES PATENTS

| | | | |
|---|---|---|---|
| 3,413,474 | 11/1968 | Frech | 250/338 |
| 3,448,268 | 6/1969 | Proctor | 250/353 |

Primary Examiner—Davis L. Willis
Attorney, Agent, or Firm—Lyon & Lyon

[57] ABSTRACT

Described herein is a method of monitoring surface resistivity distribution resulting from vacuum deposition of thin, transparent metal films on moving plastic film or other transparent substrates. The process comprises applying to the metallized film electromagnetic radiation and detecting a band width of electromagnetic radiation transmitted through or reflected from the metallized film in the near-infrared region, more particularly within the wavelength range of about 1.5 to 3.0 microns. The detected band width permits excellent correlation between emanant radiation and local conductivity or, reciprocally, resistivity of vacuum deposited gold, silver, and copper. Vacuum deposition can occur, e.g., by vacuum evaporation or sputtering. The metallized films are useful in the production of electrically heated transparent closures such as for automobile windshields.

20 Claims, 3 Drawing Figures

U.S. Patent  Jan. 27, 1976  3,935,458
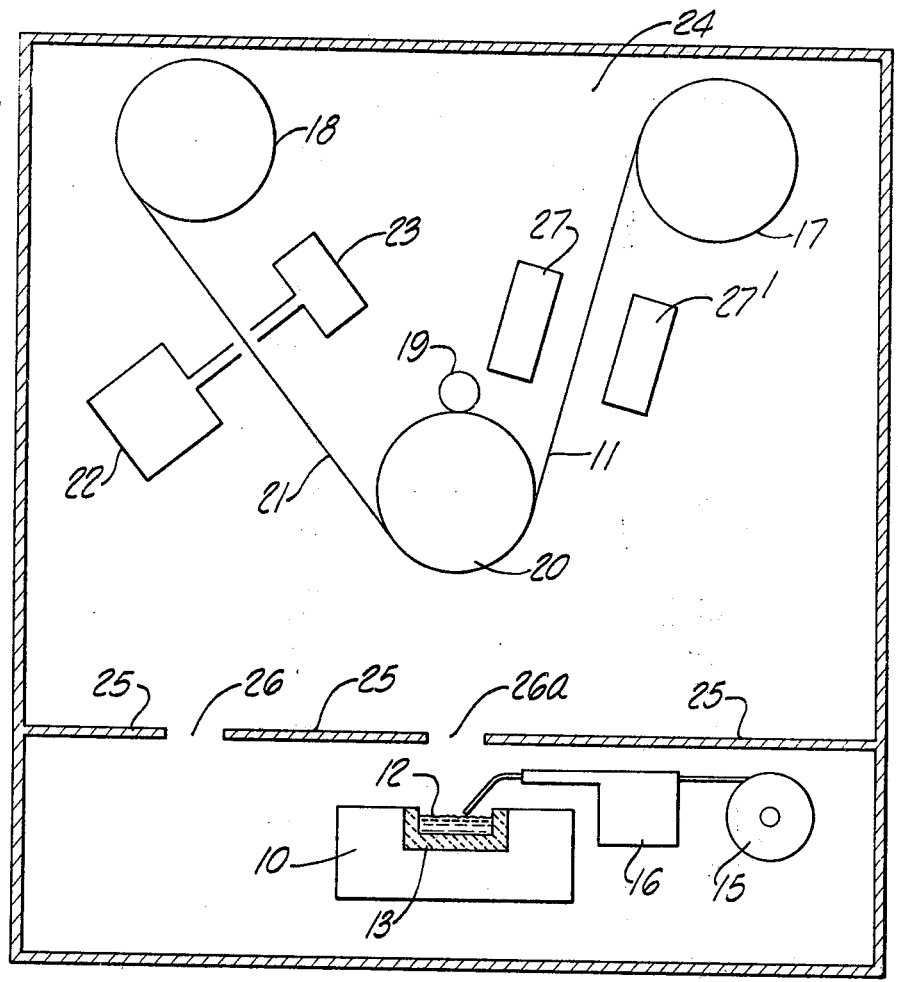
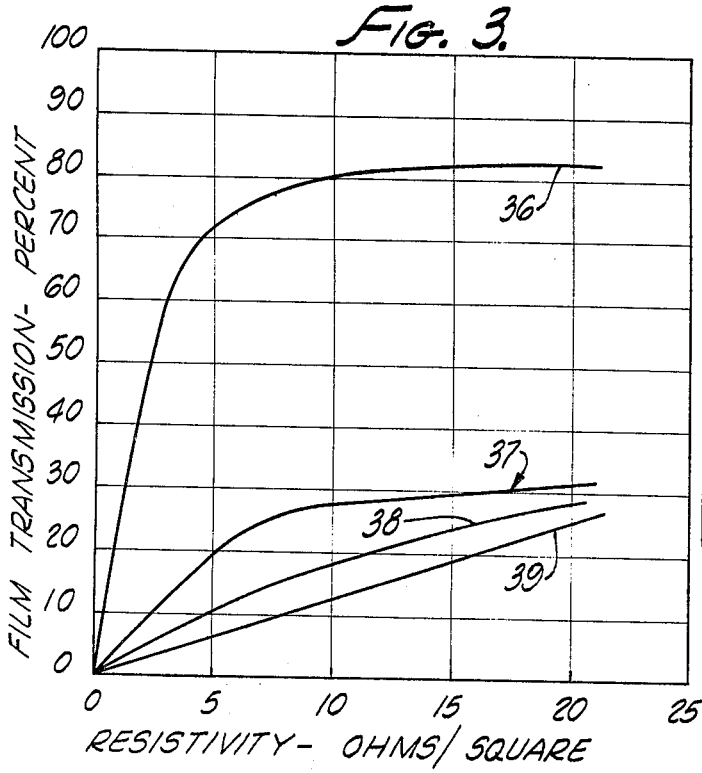
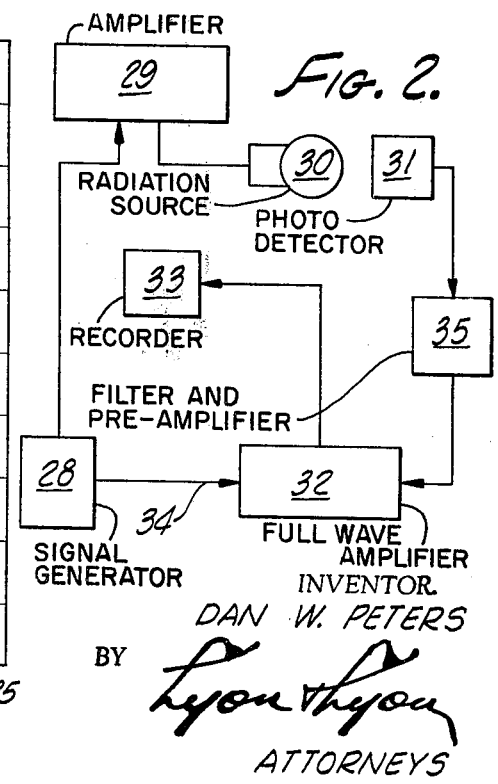
INVENTOR.
DAN W. PETERS
BY
Lyon Lyon
ATTORNEYS

METHOD FOR MONITORING THE SURFACE RESISTIVITY OF METALLIZED FILM

This is a continuation, of application Ser. No. 58,305, filed July 27, 1970, now abandoned.

FIELD OF THE INVENTION

This invention relates to a process of monitoring surface resistivity distribution of vacuum deposited metals.

BACKGROUND OF THE INVENTION

Vacuum deposited metal thin film coatings have found widespread application as transparent resistance heaters for deicing and demisting transparent enclosures such as windshields. Typically, such enclosures comprise a thin transparent plastic carrier film or substrate upon which has been deposited a thin conductive metallic film which can be powered by busbars normally attached at the edge portions thereof. Ultimately, the metallized substrate is laminated between rigid, transparent plies as of glass in order to form a safety glass-type construction.

In order that upon energizing power be dissipated in an optimal manner for the particular deicing function of the ultimate laminated transparency, and to preserve the optical properties required in windshield and like employments, resistivity distribution of the deposited metallic film must be closely controlled. In the past, local resistivity has been determined by measuring the overall (bus to bus) resistance of the final part and then normalizing the value determined to a square area configuration. This requires physical contact to a finished part already equipped with busbars. However, it is frequently desirable to determine resistivity of a metallized substrate film prior to the application thereto of busbars or other means of electrical attachment. In U.S. Pat. No. 3,086,889 to Strong, it is proposed that electrical resistance of a continuously deposited metallic coating be monitored by balancing a bridge circuit against resistance measured between electrical contacts which engage the metallic coated side of a dielectric sheet material. Unfortunately, where the metallic film whose resistance is to be measured is so thin as is the case where transparency is required, then the fragility of the metallic coating is highly susceptible to disruption by such contact methods of measurement. When the metallized film is subsequently energized, disruptions in the fragile coating give rise to localized regions of high current density which can lead to failure. Accordingly, a need has existed for a means of non-destructively describing the local resistivity of vacuum-deposited thin metal films.

In U.S. Pat. No. 3,397,672 to Dykeman, et al., it is proposed at column 3, lines 2–5, to measure the thickness of vapor-deposited aluminum by detection of radiation emanant from the coating upon application of x-rays. The equipment required for x-ray generation is generally highly expensive and to the economic disadvantages of that proposal must be added the danger to operators and maintenance personnel inevitably inhering in x-ray operation.

In determining what form of radiation will be employed and detected in monitoring resistivity of vacuum-deposited metals, however, more is involved than straightforward considerations of economy and safety. There is required a wavelength interval which when detected provides a relatively steep and linear curve of transmission or reflectance against resistivity. Moreover, where transmission is to be measured, a spectral region must be chosen wherein transmission of the bare substrate is high, i.e., a window.

BRIEF SUMMARY OF THE INVENTION

According to this invention there if provided a process of monitoring surface resistivity distribution of vacuum-deposited silver, gold, and copper on transparent plastic carrier film substrates to form transparent metallized plastic film. The process comprises applying to the metallized film electromagnetic radiation comprised of radiation having a wave length within the range of about 1.5 to 3.0 microns, and detecting a band width of radiation transmitted through or reflected from said metallized film and within the wavelength range of about 1.5 to 3.0 microns.

One object of the invention is to provide a manner of non-destructively describing the local resistivity of vacuum deposited metals.

Another object of the invention is to provide a method of sensing surface resistivity distribution of vacuum deposited gold, silver, and copper wherein the information sensed reasonably linearly correlates with actual resistivity values.

Yet another object of the invention is to provide a means of non-destructively monitoring surface resistivity distribution without resort to harmful radiation.

A further object of the invention is to monitor resistivity of metals vacuum deposited on substrate films employing a spectral region where the bare substrate transmission is high.

These and other objects and advantages of the invention will become apparent from the detailed description which follows and from the accompanying drawings in which:

FIG. 1 schematically represents a vacuum deposition apparatus environment in which the process of the invention can be practiced;

FIG. 2 schematically depicts one detection system with which the invention can be practiced; and FIG. 3 graphically correlates percent transmission of various band widths of radiation with resistivity of vacuum deposited metal on a particular substrate.

DETAILED DESCRIPTION OF THE INVENTION:

Turning now to the drawings, with particular reference to FIG. 1, there is shown an electron beam gun 10 positioned below a moving substrate 11. The electron beam of the gun is focused onto an evaporant metal 12 located in a crucible 13 recessed into electron gun 10. Evaporant metal 12 is stored in the form of wire on a spool 15. The wire is fed to crucible 13 by feed mechanism 16.

The film substrate 11 is transported from a supply reel 17 over the electron gun 10 to a take-up reel 18 by a friction roller 19 acting on driving roller 20. The friction roller 19 is connected by chains and a gear set to a reversible universal motor (not shown).

Resistivity of the metal deposit applied to substrate 11 is monitored by measuring electromagnetic radiation having a band width within the range from about 1.0 to 3.0 microns emanant from the metallized film 21. For purpose of illustration an AC energized radiation source 22 and radiation detector 23 are shown placed on either side of the metallized film 21 at a point downstream from the deposition area for measuring transmission of selected band widths of radiation. The radiation source and detector may be provided with masks to obviate the effect of stray radiation.

The vacuum deposition apparatus is contained in a vacuum chamber 24 and a wall 25 having opening 26 therein for equalization of pressure may be provided to delineate an evaporation chamber from the remainder of the vacuum chamber. Wall 25 is provided with slit 26a which can be designed to allow insertion of masks that control the size of the slip opening as to both length and width (not shown). Suitable size of the slit opening is determined by the distance between the substrate and evaporant metal 12. Slit opening length (in the direction of film travel) can be determined by the angle swept out by considering the evaporant beam to originate from a point source in the center of the crucible 13 and defining the limits as the lines tangent to driving roller 20. The width of the slip can be determined in a similar manner using as the limit the edge or width of the plastic film. Glow discharge electrodes 27 and 27' are desirably provided for surface treatment of the substrate 11 in conventional manner. Preferably, all of the substrate 11 is glow discharged prior to commencement of metal evaporation.

As will be recognized by the art skilled, deposition rate is influenced by the rate of metal evaporation, speed of film travel, nature of glow discharge treatment, source to substrate distance, and system pressure at evaporation. In the embodiment shown, glow discharge treatment occurred at 50 microns pressure of argon with power input of 1.4 KV AC and film travel speed of 6 inches per minute. For deposition, film speed was set at approximately 2 feet per minute with evaporator power setting of 0.2 kw. Source to substrate distance was fixed at 8 inches, and evaporations run at a pressure of two to five times $10^{-5}$ torr.

The techniques and apparatus for implementation of the measurement contemplated by this invention are known to those familiar with the art, but in the preferred embodiment employ an AC operated source of radiation such as an incandescent bulb having a brightness temperature greater than about 800° centigrade with a modulated driver or an optical chopper, optics directing the AC radiation through the part to be measured, and a suitable photo detector, rectifier, amplifier, and read-out device. FIG. 2 schematically illustrates one suitable system, wherein signal generator 28 supplies a signal amplified by element 29 to radiation source 30. The AC radiation is directed through the metallized substrate (not shown) and the radiation transmitted by the substrate is received by a suitably biased photo detector 31. Preferably a lead sulfide detector is employed for the band widths used in this invention, and radiation emanant from the metallized film is passed through an optical interference, bandpass filter prior to impingement upon the lead sulfide. The signal generated by detector 31 is applied through element 35 containing a filter and a 2-pole, narrow-pass pre-amplifier to a full wave rectifying power amplifier 32. At 32, the received signal is compared with a reference signal supplied by line 34 and the resulting information displayed by recorder 33.

Substrates employed in this invention are preferably transparent plastic carrier films which most preferably range in thickness from about 0.00025 to about 0.015 inch. Preferred films are cellulose triacetate, cellulose acetate, fluorinated ethylene-propylene copolymers, and polyethylene terephthalate polyester films. Among the wide variety of other suitable candidates for substrate film employment may be mentioned: cellulose acetate butyrate, cellulose propionate, ethyl cellulose, polymethylmethacrylate, polytrifluorochlorethylene copolymer, polyvinylfluoride, polycarbonate, vinylidene chloride-vinyl chloride copolymer, polyvinylchloride, vinyl chloride-acetate copolymer, and regenerated cellulose films. Of course, substrates other than transparent plastic carrier films can be employed, e.g., rigid, transparent, substrate plies as of glass, stretched polymethylmethacrylate, polycarbonate, etc. Preferably such rigid plies range in thickness from about 0.02 to 0.25 inches. The metals deposited on the substrate films are selected from the group consisting of silver, gold, and copper and are generally deposited in thicknesses within the range from about 100 to 500 angstroms. The resulting resistivity of the deposited metal generally is within the range from about 10 to about 25 ohms per square.

Both the substrate film and the metal coating deposited thereon are transparent in the sense that visible light is transmitted therethrough without appreciable scattering such that objects beyond are clearly visible. Preferably, the metallized film exhibits luminous light transmission greater than about 20 percent, and most preferably greater than about 70 percent.

As has been noted hereinabove, detected wavelengths within the range from about 1.5 to 3.0 microns have been discovered to provide a high level of correlation with resistivity of vacuum-deposited gold, silver, and copper. At wavelengths less than about 1.5 micron the requisite slope and relative linearity of the percent transmission-resistivity curve is seldom obtained. Detector respose falls off rapidly between 3 and 4 microns, and the metal films at greater wavelengths appear to exhibit uniform reflection regardless of resistivity. Best results have been obtained when operating at wavelengths between about 1.5 and 2.0 microns, most preferably 1.8 microns. FIG. 3 depicts the relationship of percent transmission of various detected band widths to resistivity of gold vacuumdeposited on a fluorinated ethylene-propylene film. Curve 36 represents percent transmission of white light as detected by a cadmium sulfide detector as a function of resistivity. Curves 37, 38, and 39, respectively, illustrate transmission as a function of resistivity for detected band widths centered about 1.0, 1.5, and 2.0 microns. The latter three curves were drawn from data taken by spectrophotometer readings. Curves 36, 37, 38, and 39 were constructed by (1) measuring the IR transmission through substrate films bearing metal coatings of various densities and (2) cutting square portions of the coated substrate which include the IR measured region, attaching busbars thereto, and measuring resistance directly with a DC ohm-meter. The correlative advantage to be gained by practice of the invention in terms of linearity and slope of the transmission-resistivity curve will be apparent from FIG. 3. The criticality of the wavelength interval employed in this invention will become apparent when it is considered that curve 37 throughout much of its length exhibits slope no greater than that for white light, notwithstanding that the wavelength detected for curve 37 is but 0.5 micron less than that for curve 38. With gold deposited on a cellulose triacetate substrate, transmission versus resistivity curves have been obtained which are linear between 8 and 20 ohms per square with a slope, in this range, of 0.83 percentage point of transmission per ohm per square, i.e., 12 percent to 20 percent transmission corresponding to from 8 to 20 ohms per square. With polyethyleneterephthalate polyester film transmission versus resistivity slope of 1.72 percentage point per ohm per square over a range of 9 to 20 ohms per square corresponding to 23 to 42 percent transmission has been obtained by detection of a band width transmitted radiation at a wavelength interval centered at 1.8 microns. In that wavelength interval, transmission of the bare substrate is extremely high, i.e., 92 percent transmission in vacuum.

In the preferred embodiment, the radiation detected is radiation transmitted through the metallized substrate. Of course, the art-skilled will recognize that the invention can also be practiced by detecting reflected radiation, in which instance the included angle of reflection should be as narrow as possible in view of the demonstrated tendency of all wave lengths of radiation to be reflected at low grazing angles. Indeed, resort can be had to conventional optical arrangements to provide that the included angle of reflection be zero degrees. While the invention can be employed to detect reflected radiation, preferably the detected radiation is transmitted radiation. Slight torsional movement of the film during transport, with resultant deviation of reflected radiation, can displace the signal beam from the view of the detector, falsely simulating variations in the intrinsic reflectivity of the coated film. For this reason, systems operating in the reflective mode require more elaborate detector optics, such as field lens systems, to assure uniform irradiation of the detector during torsional substrate film movement and attendant signal beam deviation.

The invention has been described hereinabove with particular reference to vacuum evaporation techniques of metal deposition. Of course, the art-skilled will recognize that other means of deposition can be employed. As an example of other suitable methods can be mentioned sputtering, wherein residual gases contained in a vacuum chamber are ionized by application of high voltage. The ions are accelerated toward an electrode comprised of the metal to be deposited. When the accelerated ions strike the electrode, their accumulated energy dislodges metal particles from the electrode which are subsequently deposited on the substrate film. In the light of this specification, of course, other means of metal deposition will occur to the art skilled.

Similarly, the art skilled will recognize that DC detection systems can be employed in lieu of the AC system exemplified above. With DC detector systems, expensive signal generators and amplifiers are supplanted by inexpensive batteries and DC voltmeters. However, the DC detector system is subject to a temperature drift effect, so that cooling or other suitable means of alleviating this effect should be provided.

From the foregoing, it will be clear to the art skilled that the method of this invention is suitable for diverse employments. For example, the invention can be employed as a quality control or inspection process with discrete coated parts. Alternatively, the method of the invention can be employed to monitor batch coating of individual parts so that deposition is permitted to proceed until a predetermined value of resistivity has been achieved, at which time the deposition apparatus can be switched off automatically and prepared for removal of the coated part and installation of the next part to be coated. Similarly, the invention is applicable to continuous or semicontinuous vacuum metallizing processes wherein the metallic deposit is applied to a moving substrate, such as a film web, which moves continuously or semi-continuously past the point of deposition. In this configuration, radiation transmitted through or reflected from the metallized film is monitored at a point immediately following that of deposition and the value of the detected radiation, or monitor signal, can be compared with a predetermined set point or standard value to generate an error signal. The error signal can be employed to control rate of film transport, power to the electron gun, rate of feed to the electron gun crucible, or otherwise control evaporation or deposition rate in order to achieve an extended deposit having local resistivity values within specified limits.

Having fully described the invention, it is intended that it be limited only to the legal scope of the claims appended hereto.

I claim:

1. A process useful in monitoring the surface resistivity distribution of the deposit obtained by the vacuum deposit of a metal selected from the group consisting of silver, gold and copper on a transparent plastic film carrier to form a metallized plastic film having luminous light transmission greater than about 20 percent comprising applying electro-magnetic radiation comprised of radiation within the wavelengths of about 1.5 to 3.0 microns to the metallized film, detecting a signal corresponding to a wavelength interval of electro-magnetic radiation within the range of about 1.5 to 3.0 microns transmitted through said film and deposit, and correlating the value of the detected signal to the surface resistivity of the film.

2. The process of claim 1 wherein the carrier film has a thickness within the range of about 0.00025 to 0.015 inch and wherein the said deposit exhibits resistivity in the range from about 5 to 50 ohms per square.

3. The process of claim 2 wherein the said deposit exhibits resistivity in the range from about 10 to 25 ohms per square.

4. The process of claim 3 wherein the source of applied radiation is an incandescent source having a brightness temperature greater than about 800°C.

5. The process of claim 4 wherein the carrier film is selected from the group consisting of cellulose acetate, cellulose triacetate, fluorinated ethylene-propylene copolymer, and polyethylene terephthalate-polyester films.

6. The process of claim 5 wherein the carrier film is polyethylene terephthalate polyester film.

7. The process of claim 6 wherein the vacuum deposited metal is gold.

8. The process of claim 7 wherein the detected radiation is radiation having a wave length of about 1.8 microns.

9. The process of claim 5 wherein the metalized plastic film has integrated visible light transmission greater than about 70 percent.

10. The process of claim 9 wherein the metalized plastic film has integrated visible light transmission greater than about 70 percent.

11. A process according to claim 1 wherein the percent transmission of the applied radiation through the film and deposit is determined from the value of the detected signal and the percent transmission correlated to the surface resistivity of the film.

12. A process according to claim 11 wherein the carrier film has a thickness range of about 0.00025 to 0.015 inch and wherein the said deposit exhibits resistivity in the range from about 5 to 50 ohms per square.

13. A process according to claim 1 wherein the detected signal is compared with a reference signal and the resulting information displayed on a recorder.

14. A process of determining surface resistivity of the deposit formed by vacuum deposition of a metal selected from the group consisting of silver, gold and copper on a transparent substrate to form a transparent metalized member having luminous light transmission greater than about 20 percent which process comprises applying to the metalized member electromagnetic radiation comprised of radiation within the wave length of about 1.5 to 3.0 microns, detecting a signal corresponding to a wave length interval of electromagnetic radiation transmitted through said substrate and deposit and within the range of about 1.5 to 3.0 microns, determining the percent transmission of the applied radiation through the film and deposit from the value of the detected signal and correlating the percent transmission to the surface resistivity of the deposit.

15. In a process for the preparation of transparent metalized film having luminous light transmission greater than 20 percent, by the vacuum deposition of a metal selected from the group consisting of silver, gold and copper on a transparent plastic carrier film, the improvement comprising monitoring of the surface resistivity distribution of the deposit formed on the film by applying electromagnetic radiation within the wave length of about 1.5 to 3.0 microns to the film and deposit, detecting a signal comprising a wave length interval of electromagnetic radiation within the range of about 1.5 to 3.0 microns transmitted through the film and deposit, and correlating the value of the signal to the surface resistivity distribution of the deposit on the film.

16. A process according to claim 15 wherein the deposition of the metal on the carrier film proceeds until a predetermined value of resistivity has been achieved.

17. The process according to claim 15 wherein the metal is deposited on a moving transparent film and the electromagnetic radiation is applied at a point immediately following that of deposition of the metal.

18. The process according to claim 17 wherein the value of the detected signal is compared with a predetermined value to generate an error signal.

19. A process according to claim 18 wherein the error signal is employed to control the amount of metal deposited on the film so as to achieve resistivity value from about 10 to 25 ohms per square.

20. A process according to claim 18 wherein the error signal is employed to control the rate of deposition of metal of the film in order to achieve an extended deposit having local resistivity values within specified limits.

* * * * *